United States Patent [19]
Suzuki et al.

[11] Patent Number: 5,225,783
[45] Date of Patent: Jul. 6, 1993

[54] DIELECTRIC CONSTANT DETECTION APPARATUS FOR FUEL

[75] Inventors: Hiroyoshi Suzuki; Kenji Ogawa; Akira Okada, all of Himeji, Japan

[73] Assignee: Mitsubishi Denki Kabushiki Kaisha, Tokyo, Japan

[21] Appl. No.: 826,392

[22] Filed: Jan. 27, 1992

[30] Foreign Application Priority Data

Feb. 18, 1991 [JP] Japan ................... 2-022488
Feb. 18, 1991 [JP] Japan ................... 2-022489

[51] Int. Cl.$^5$ ............................................. G01R 27/26
[52] U.S. Cl. ................... 324/655; 73/61.61; 324/668
[58] Field of Search ............... 324/655, 657, 668, 681, 324/682; 73/61.43, 61.61; 328/155; 307/262

[56] References Cited

U.S. PATENT DOCUMENTS

| | | | |
|---|---|---|---|
| 3,436,647 | 4/1969 | Gobeli et al. ................ | 328/155 |
| 4,023,116 | 5/1977 | Altke et al. .................. | 328/155 |
| 4,055,814 | 10/1977 | Abraham et al. .............. | 328/155 |
| 4,599,888 | 7/1986 | Hufton et al. . | |
| 4,675,596 | 6/1987 | Smith ......................... | 324/683 |
| 4,820,972 | 4/1989 | Scott et al. .................. | 324/158 P |
| 4,835,481 | 5/1989 | Geissler et al. .............. | 328/155 |
| 4,847,569 | 7/1989 | Dudziak et al. .............. | 328/155 |
| 4,888,824 | 12/1984 | Andersen et al. ............. | 324/668 |
| 5,119,671 | 5/1992 | Kopera ....................... | 324/655 |

FOREIGN PATENT DOCUMENTS 1-132985 5/1989 Japan .
3-35620 5/1991 Japan .

OTHER PUBLICATIONS

IBM Technical Disclosure Bulletin vol. 14 No. 4 Sep. 1971 Sensor Circuit Utilizing Inductance Input, Orgen.
Western Electric Technical Digest No. 33 Jan. 1974 A Circuit for Determining Resonance Frequency and Effective Series Resistance of an Induction-Capacitor Network Mosher.
Patent Abstracts of Japan, unexamined applications, p field, vol. 4, 95, Jul. 9, 1980.

Primary Examiner—Kenneth A. Wieder
Assistant Examiner—Maura K. Regan
Attorney, Agent, or Firm—Sughrue, Mion, Zinn, Macpeak and Seas

[57] ABSTRACT

A detection apparatus for detecting a dielectric constant of fuel having an electrode disposed in a fuel passage and applied with an excitation signal, a monolayer-wound coil disposed in the vicinity of the electrode so that fuel is introduced in a space between the excitation electrode and the coil, a phase comparator which receives the signal to be applied to the excitation electrode and a signal induced in the coil to thereby compare the signals. The phase difference between both signals is detected using a low-pass filter to output the d.c. signal component of an output signal of phase comparator, a comparison integrator connected to the low-pass filter to output a controlled output signal so that the phase difference between the excitation signal and the induced signal in the coil becomes 90°, and a voltage controlled oscillator connected to the comparison integrator so that the frequency of a signal, to be applied to the electrode, of the voltage controlled oscillator is changed depending on the output signal of the comparison integrator. The dielectric constant of the fuel is detected on the basis of a voltage output signal from the comparison integrator, or a frequency output signal from the voltage controlled oscillator.

3 Claims, 8 Drawing Sheets

FIGURE 11 *PRIOR ART*
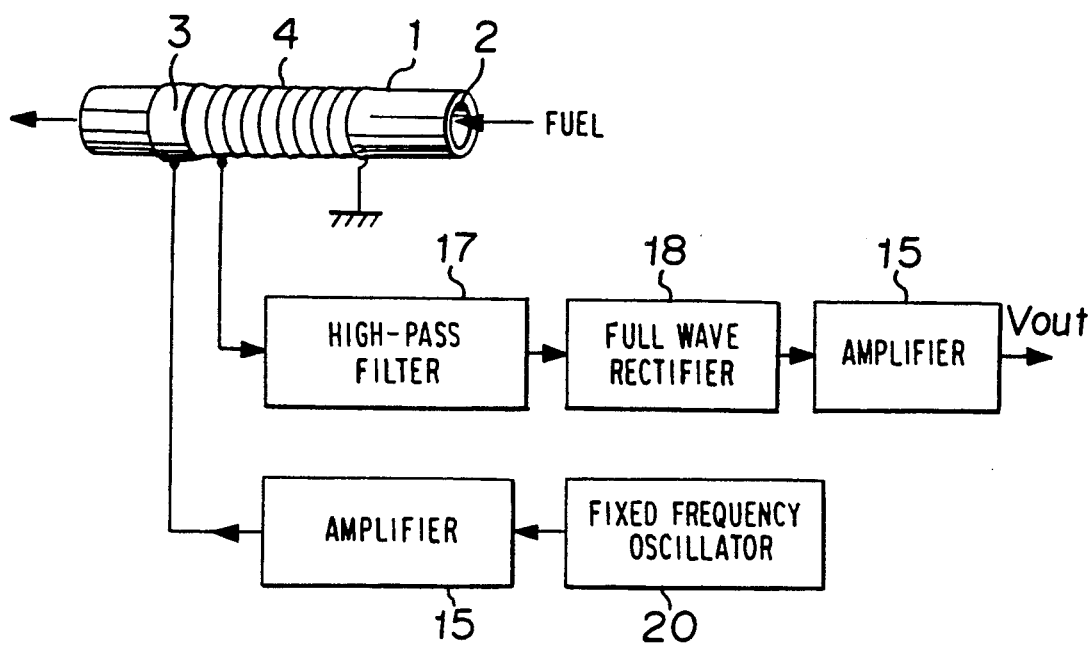
FIGURE 12 *PRIOR ART*
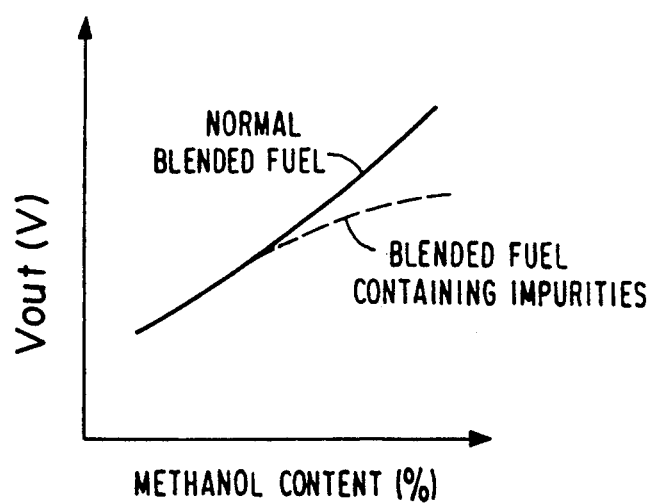

DIELECTRIC CONSTANT DETECTION APPARATUS FOR FUEL

BACKGROUND OF THE INVENTION

The present invention relates to a dielectric constant detection apparatus for fuel which detects a dielectric constant of fuel supplied to a burner or the like in a non-contact state to thereby detect the property of the fuel. More particularly, it relates to such apparatus to measure the alcohol content of an alcohol blended fuel used for the engine of an automobile.

Fuel in which alcohol is blended in gasoline has been used for automobiles to thereby reduce consumption of oil and to reduce air pollution due to exhaust gas from automobiles in the U.S.A. and European countries. When the alcohol blended fuel is used for an automobile engine which is adjusted regarding an air fuel ratio of gasoline, the air-fuel ratio becomes lean because the theoretical air-fuel ratio of alcohol is smaller than that of the gasoline, whereby it is difficult to obtain stable driving. Accordingly, the alcohol content of the alcohol blended fuel is detected to thereby adjust the air fuel ratio, ignition timing and so on. Thus, adjustment is made on the basis of a detected value.

In order to detect the alcohol content, there have been proposed a system of detecting the dielectric constant of alcohol blended fuel and a system of detecting the refractive index of the fuel. As a conventional apparatus used for the system of detecting the dielectric constant of the alcohol blended fuel, such one as disclosed in Japanese Examined Patent Publication No. 31734/1988 was utilized to detect the dielectric constant of the fuel in a non-contact state. Now, description will be made with reference to FIGS. 3, 11 and 12 as to a case that the detection apparatus is used for detecting an alcohol content in alcohol blended fuel.

FIG. 11 is a diagram showing the conventional detection apparatus for detecting a dielectric constant of fuel, wherein reference numeral 1 designates an insulation tube made of an insulation material such as ceramics, oil-resisting plastics or the like and in which a fuel passage 2 is formed, numeral 3 designates an electrically conductive electrode wound in a ring form on a part of the insulation tube 1, and numeral 4 designates a monolayer-wound coil wound on the insulation tube 1 so as to be apart from the electrode 3 by a predetermined distance. A sensor member is formed of the above-mentioned elements 1 through 4. Reference numeral 20 designates a fixed frequency oscillator to apply a voltage signal having a fixed frequency to the electrode 3 through an amplifier 15. The coil 4 has a terminal grounded and the other terminal through which a signal is outputted as an output $V_{out}$ through a high-pass filter 17, a full wave rectifier 18 and the amplifier 15.

FIG. 3 is a diagram showing the frequency characteristics of the sensor member in which there are shown voltages induced in the coil 4 and the change of the phases of the induced voltage signals by the induced signals of the electrode 3 in a case that gasoline (line a) and methanol (line b) are used as fuel, and the frequency is changed while a voltage applied to the electrode 3 is constant. FIG. 12 is a diagram showing the output characteristics of the conventional apparatus in which an output $V_{out}$ to a methanol content of fuel in the conventional apparatus is shown in a case that a signal having a fixed frequency of as shown in FIG. 3 is supplied to the electrode 3 from the fixed frequency oscillator 20.

The operation of the conventional apparatus will be explained.

In FIG. 11, when a frequency applied to the electrode 3 is changed, a voltage induced in the coil 4 shows the maximum value at a different frequency in a case of a different dielectric constant of fuel. It is because LC (inductance-capacitance) resonance is resulted due to a capacitance Cf corresponding to a dielectric constant e of fuel between the electrode 3 and the coil 4 and the self-inductance L of the coil 4, whereby the induced voltage of the coil becomes maximum at the resonance frequency. The resonance frequency f is expressed by the following formula:

$$f = k/\sqrt{\{L \times (Cf + Cs)\}} = k/\sqrt{(a + b \times \epsilon)} \quad (1)$$

where Cs represents the capacitance of a monolayer-wound coil and k, a and b are respectively constants determined by the shape of the sensor member. Since the resonance frequency f depends on the dielectric constant $\epsilon$ of the fuel as shown in the above-mentioned formula, the resonance frequency decreases as the dielectric constant $\epsilon$ becomes large. For instance, in the measurements of the resonance frequency with use of a sensor member having a specified shape, it was found that the resonance frequency fm was about 5 MHz for methanol having a dielectric constant $\epsilon$ of 33 and the resonance frequency fg was about 5.7 MHz for gasoline having a dielectric constant e of 2. In view of the above, when methanol blended gasoline is introduced in the fuel passage 2 in FIG. 11 and a signal having a frequency of which is slightly higher than the resonance frequency fm is generated from the fixed frequency oscillator 20 to thereby excite the electrode 3 at a fixed voltage through the amplifier 15, only an a.c. component in the voltage signal induced in the coil 4 is extracted by the high-pass filter 17. The a.c. component is subjected to full wave rectification in the full wave rectifier 18 and the amplitude of the alternating current is detected. The detected amplitude is adjusted to have a predetermined voltage range by the amplifier 15 and the adjusted signal is outputted. Thus, the induced voltage having the frequency of becomes large as the methanol content is large (FIG. 3). Accordingly, the output $V_{out}$ is substantially proportional to the methanol content as shown in FIG. 12.

The conventional apparatus, however, had the disadvantage as follows. When impurities having a high electric conductivity, e.g. metal ions resulted from broken pieces of a fuel distribution system, rust or the like are mixed in fuel, or a slight amount of an ion series additive for fuel, rain water or the like invades in it, the output $V_{out}$ shows a remarkable change even though the dielectric constant $\epsilon$, i.e. the methanol content, is not substantially changed, as indicated by a broken line b' in FIG. 3. This is because the Q factor of LC resonance decreases due to an increased electric conductivity of fuel, and the induced voltage is greatly reduced at the same frequency fo. Further, when temperature and humidity in the atmosphere around the sensor member change, the insulation resistance between the electrode 3 and the coil 4 is changed, and accordingly, there causes a change of the output. Because of a change of the electric conductivity between the electrode 3 and the coil 4 due to a slight amount of impurities or a change in the atmosphere around the sensor member, it is difficult to detect correctly the methanol content.

SUMMARY OF THE INVENTION

It is an object of the present invention to provide an electric constant detection apparatus capable of detecting an alcohol content with a high accuracy even when impurities are mixed in the fuel.

In accordance with the present invention, there is provided a detection apparatus for detecting a dielectric constant of fuel which comprises an electrically conductive electrode disposed in a fuel passage and applied with an excitation signal, a monolayer-wound coil disposed in the vicinity of said excitation electrode so that fuel can be introduced in a space between said electrode and said coil, a phase comparator which receives the excitation signal to be applied to said electrode and an induced signal in said coil to thereby compare the signals, whereby the phase difference between the both signals is detected, a low-pass filter to output the d.c. signal component of an output signal of the phase comparator, a comparison integrator connected to said low-pass filter to output a controlled output signal so that the phase difference between the excitation signal to be applied to said electrode and the induced signal in the coil becomes 90°, and a voltage controlled oscillator connected to said comparison integrator so that the frequency of a signal, to be applied to said electrode, of the voltage controlled oscillator is changed depending on the output signal of said comparison integrator, whereby the dielectric constant of the fuel is detected on the basis of a voltage output signal from said comparison integrator, or a frequency output signal from said voltage controlled oscillator. In accordance with the present invention, there is provided a detection apparatus for detecting a dielectric constant of fuel which comprises an electrically-conductive electrode disposed in a fuel passage, a monolayer-wound coil disposed apart from said electrode by a predetermined distance so that the cylindrical face of said coil opposes said electrode, and fuel can be introduced in a space between said electrode and said coil, a resistor connected in series to said coil to thereby form a series circuit, a signal application means for applying a high frequency signal to said series circuit, a phase comparator which receives a signal appearing at the connecting portion of said coil and said resistor and the high frequency signal to be applied to the series circuit to thereby compare both signals, whereby the phase difference between both signals is detected, a low-pass filter to output the d.c. signal component of an output signal of the phase comparator, a comparison integrator connected to said low-pass filter to output a controlled output signal so that the phase difference between the signal appearing at the connecting portion of said coil and said resistor, and the high frequency signal to be applied to said series circuit becomes 0°, and a voltage controlled oscillator connected to said comparison integrator so that the frequency of the high frequency signal to be applied to said series circuit is changed depending on the output signal of said comparison integrator, whereby the dielectric constant of the fuel is detected on the basis of a voltage output signal of said comparison integrator, or a frequency output signal of said voltage controlled oscillator.

BRIEF DESCRIPTION OF THE DRAWINGS

In the drawings:

FIG. 11 is a diagram showing a conventional dielectric constant detection apparatus for fuel; and FIG. 12 is a output characteristic diagram of the conventional apparatus.

DETAILED DESCRIPTION OF THE PREFERRED EMBODIMENTS

Preferred embodiments of the present invention will be described with reference to the drawings.

Figure 1:
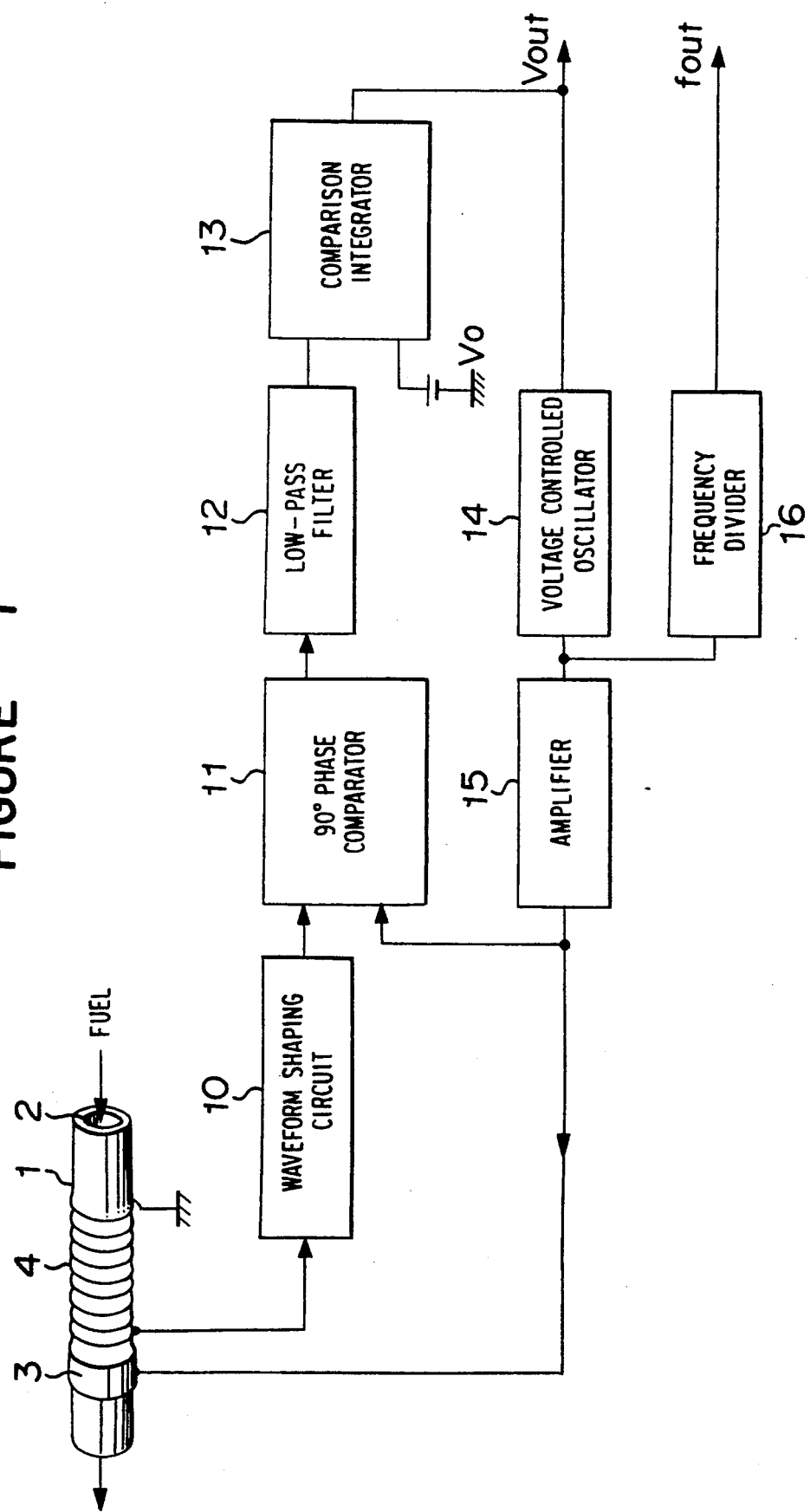
FIG. 1 is a diagram showing an embodiment of the dielectric constant detection apparatus for fuel according to the present invention.

FIG. 1 is a diagram showing an embodiment of the dielectric constant detection apparatus for fuel according to the present invention, wherein a sensor member formed of elements indicated by reference numerals 1–4 is the same as that of the above-mentioned conventional apparatus. Reference numeral 10 designates a waveform shaping circuit to which a terminal of the monolayer-wound coil 4 is connected, numeral 11 designates a 90° phase comparator to which the output of the waveform shaping circuit 10 and an excitation signal to be supplied to the electrically conductive electrode 3 are inputted, numeral 12 designates a low-pass filter to receive an output from the 90° phase comparator, numeral 13 designates a comparison integrator to which the output of the low-pass filter 12 and a given reference voltage corresponding to a phase of 90° are inputted, numeral 14 designates a voltage controlled oscillator to which the output of the comparison integrator 13 is connected, and numeral 15 designates an amplifier to amplify the output of the voltage controlled oscillator 14. The output of the amplifier is connected to the excitation electrode 3. Numeral 16 designates a frequency divider for dividing an output frequency in a signal from the voltage controlled oscillator 14.

The function of the above-mentioned embodiment of the present invention will be described. When fuel is introduced in the fuel passage 2 and the frequency of an signal to be applied to the electrode 3 is changed in FIGS. 1 and 3, an induced voltage is resulted in the coil 4. At this moment, the phase difference between the excitation signal and the induced voltage signal is 90° at the LC resonance frequency resulted from the capacitance Cf of the fuel between the electrode 3 and the coil 4 and the inductance L of the detection coil 4. And at the same time, the induced voltage exhibits the maximum value. Further, the phase difference rapidly changes from 180° to 0° at the above-mentioned resonance frequency.

Since the capacitance Cf depends on the dielectric constant $\epsilon$ of the fuel passed in the fuel passage 2 between the electrode 3 and the detection coil 4, the resonance frequency, i.e. the frequency at which the phase difference becomes 90° is decreased as the dielectric constant e of the fuel becomes large. Such resonance frequency changes depending on the shape of the sensor member, for instance, the diameter and the wall thickness of the insulation tube 1, the distance between the electrode 3 and the detection coil 4, the inductance L of the coil 4 and so on. Measurements were made by using a sensor member having a specified shape. As a result, when methanol having a dielectric constant $\epsilon=33$ was used as fuel, the resonance frequency fm was about 5 MHz, and when gasoline of a dielectric constant $\epsilon=2$ was used, the resonance frequency fg was about 5.7 MHz. Accordingly, when methanol blended gasoline is introduced in the fuel passage 2 and the methanol content is increased, the frequency at which the phase difference becomes 90° is successively changed from about 5.7 MHz to about 5 MHz.

Explanation will be made in more detail as to a method of detecting the above mentioned resonance frequency with reference to FIG. 1.

When the methanol blended gasoline is introduced in the fuel passage 2, and an excitation signal is supplied from the amplifier 15 to the electrode 3, an induced voltage signal resulted in the coil 4 varies depending on the frequency of the induced signal. At this moment, Q of the detection element is fairly high even in a state that the fuel contains impurities. Accordingly, the induced voltage signal resulted in the coil 4 becomes a sine wave even when the induced signal applied to the electrode 3 has a rectangular waveform. Accordingly, it is unnecessary for the voltage controlled oscillator 14 to be a sine wave oscillator, but it is sufficient for it to be a rectangular wave oscillator. Further, in this case, the amplifier 15 can be a digital logical buffer.

The induced voltage signal in the coil 4 is inputted to the waveform shaping circuit 10 in which the signal is subjected to waveform shaping. The excitation signal to be applied to the electrode 3 and the output signal of the waveform shaping circuit 10 are inputted to the 90° phase comparator 11 in which the phase of the two signals are compared, whereby the phase comparator 11 generates a signal which corresponds to the phase difference of the two signals. When the excitation signal and the output signal of the waveform shaping circuit 10 have a rectangular waveform, the phase comparator 11 may be an exclusive OR circuit. Further, a digital logical circuit may be utilized for the waveform shaping circuit 10.

Then, the output signal of the phase comparator 11 is converted into a d.c. voltage signal by the low-pass filter 12. The comparison integrator 13 performs comparison and integration of the reference voltage which corresponds to a phase of 90° of the signal from the low-pass filter 12 and the output of the low-pass filter 12, and the voltage output of the comparison integrator 13 is supplied to the voltage controlled oscillator 14, whereby the frequency of the excitation signal to be applied to the electrode 3 through the amplifier 15 is determined. Namely, the oscillation frequency of the voltage controlled oscillator 14 is controlled so that the phase difference of the excitation signal of the electrode 3 and the induced voltage signal of the coil 4 is 90° by means of a phase-synchronizing loop. Accordingly, the voltage output $V_{out}$ of the comparison integrator 13 or the frequency output of the voltage controlled oscillator 14 corresponds to the resonance frequency of the sensor member, i.e. the electric constant $\epsilon$ of the fuel, or, in other words, a value corresponding to the methanol content.

Figure 3:
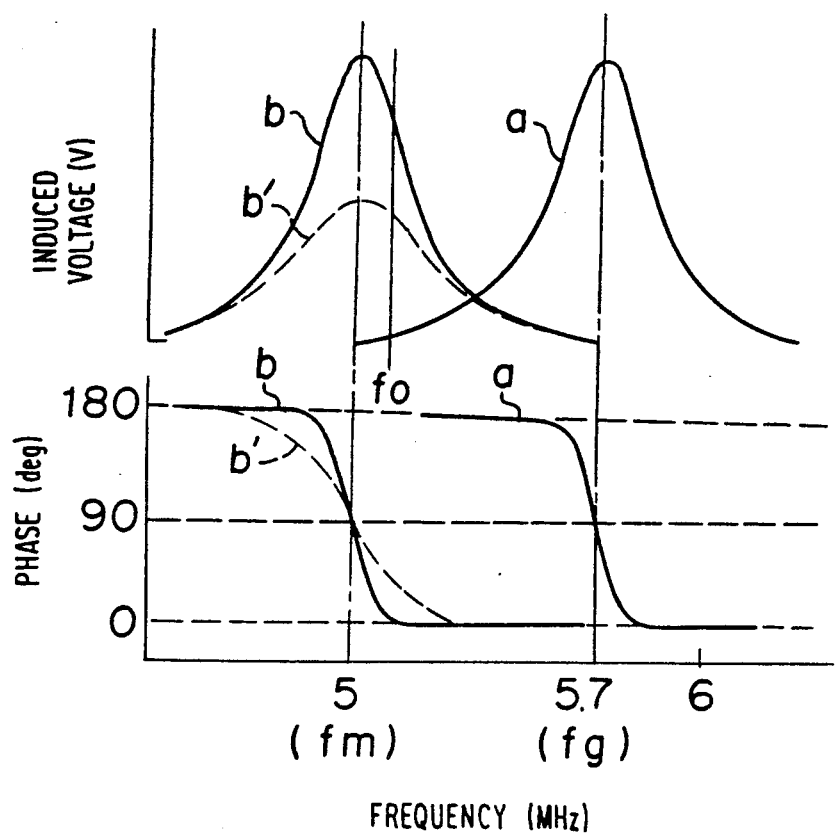
FIG. 3 is a diagram showing the frequency characteristics of a sensor member used for the present invention.

Since the frequency output of the voltage controlled oscillator is a harmonic wave of several MHz, as explained with reference to FIG. 3, it is divided by means of the frequency divider 16 so that a divided frequency becomes a frequency suitable for measurement of an output, and a signal having a suitable frequency is outputted as $f_{out}$.

Figure 4A:
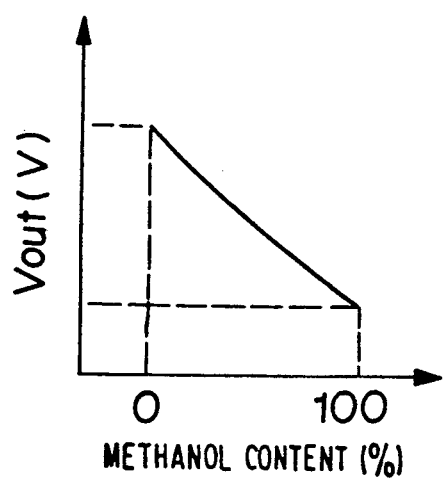
FIGS. 4a and 4b are respectively diagrams showing relations of alcohol content to outputs in accordance with the present invention.
Figure 4B:
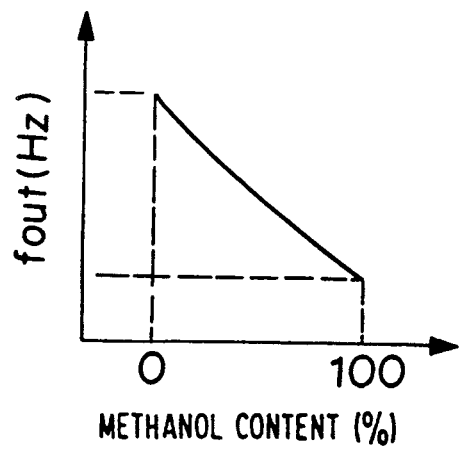

FIG. 4a shows a relation of the voltage output $V_{out}$ of the comparison integrator 13 to alcohol content in the above-mentioned embodiment, and FIG. 4b shows a relation of the frequency output $f_{out}$ of the frequency divider 16 to the alcohol content of the embodiment. The Figures show that when the methanol content is increased, i.e., the dielectric constant e is increased, the outputs are linearly decreased.

In the above-mentioned construction of the embodiment, even when the Q factor is decreased because of an increased electric conductivity of fuel due to impurities in the fuel, reduction in the insulation resistance between the electrode 3 and the coil 4 due to a change in temperature or humidity, there is no substantial influence to the frequency at the resonance point at which the phase difference between the excitation signal and the induced voltage signal becomes 90°, and accordingly, there is no change of output unlike the conventional apparatus.

Figure 2:
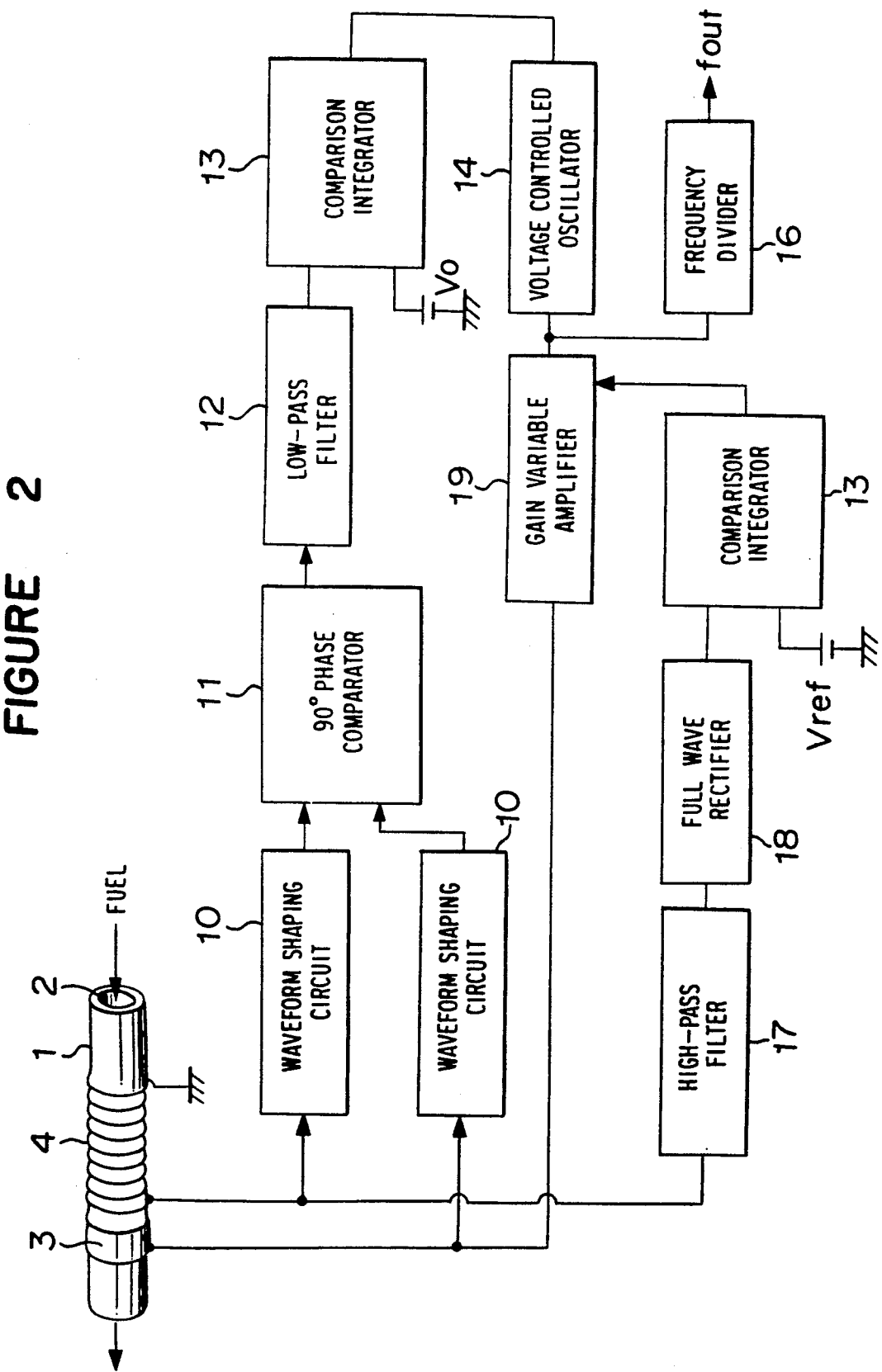
FIG. 2 is a diagram showing another embodiment of the dielectric constant detection apparatus according to the present invention.

FIG. 2 is a diagram showing another embodiment of the dielectric constant detection apparatus for fuel according to the present invention. In FIG. 2, the same reference numerals as in FIG. 1 designate the same elements. Reference numeral 17 designates a high-pass filter to which a terminal of the coil 4 is connected, numeral 18 designates a full-wave rectifier connected to the high-pass filter 17, and numeral 19 designates a variable gain amplifier which receives a signal from the comparison integrator 13 and changes the amplification gain in response to the value of the input signal. In such construction, an excitation signal to be applied to the electrode 3 and an induced voltage signal detected by the coil 4 are subjected to waveform shaping in the waveform shaping circuit 10. In the same manner as the embodiment 1, a phase synchronizing loop is formed of the 90° phase comparator 11, the low-passed filter 12, the comparison integrator 13 and the voltage controlled oscillator 14, and feedback control is performed for the frequency of the excitation signal so that the phase difference between the excitation signal and the induced voltage signal becomes 90°. As a result of the feedback control, a frequency output is provided through the frequency divider 16.

The alternating current component of the induced voltage signal of the coil 4 is extracted by the high-pass filter 17. The alternating current component is converted into a direct current output which corresponds to the amplitude of the alternating current component by the full-wave rectifier 18. The direct current output is compared at the comparison integrator 13 with a voltage $V_{ref}$ which corresponds to a predetermined reference amplitude. With the output of the comparison integrator 13, the amplification factor of the excitation signal of the gain variable amplifier 19 can be changed. Namely, in this embodiment, since the induced voltage signal of the coil 4 is always kept to have a constant amplitude, matching can be smooth. Further, the resonance frequency can be always detected correctly even when the Q varies due to change in the content of the impurities in the fuel and change in the atmosphere around the sensor member. Accordingly, the accuracy of the output can be improved.

Further, since the frequency range of the induced voltage signal can be restricted in the range of the detected electric conductivity $\epsilon$, it is preferable to use a bandpass filter, which allows only such range of frequency to pass, as the high-pass filter 17 in view of improvement of the S/N ratio.

In the first and second embodiments, although the 90° phase comparator 11 is used as a phase comparator, either of the excitation signal or the induced voltage signal to be supplied to the phase comparator may be inputted to a 90° phase shifter to shift the phase, and the phase of the signal may be compared in a 0° phase comparator such as a multiplier.

Further, in the above-mentioned embodiments although the detection apparatus of the present invention is used for detecting the methanol content of a methanol blended fuel, it can be widely used for detecting a dielectric constant of liquid generally.

Thus, in accordance with the embodiments of the present invention, an electrode and a monolayer-wound coil are disposed in a fuel passage, between which fuel is passed; an excitation signal is applied to the electrode; the phase of the output signal of the coil is caused to have a phase difference of 90° with respect to the phase of the excitation signal; then, both signals are compared in a 90° phase comparator; the output of the phase comparator is successively inputted to a low-pass filter, a comparison integrator and a voltage controlled oscillator by which the frequency of the excitation signal undergoes a feedback control, and the alcohol content of the fuel is detected on the basis of the frequency of the excitation signal. Accordingly, the alcohol content can be detected with high accuracy regardless of increase of the electric conductivity of fuel due to impurities contained in the fuel or change of temperature and humidity of the atmosphere surrounding the sensor member.

The third embodiment of the present invention will be described with reference to FIGS. 5 through 7.

Figure 5:
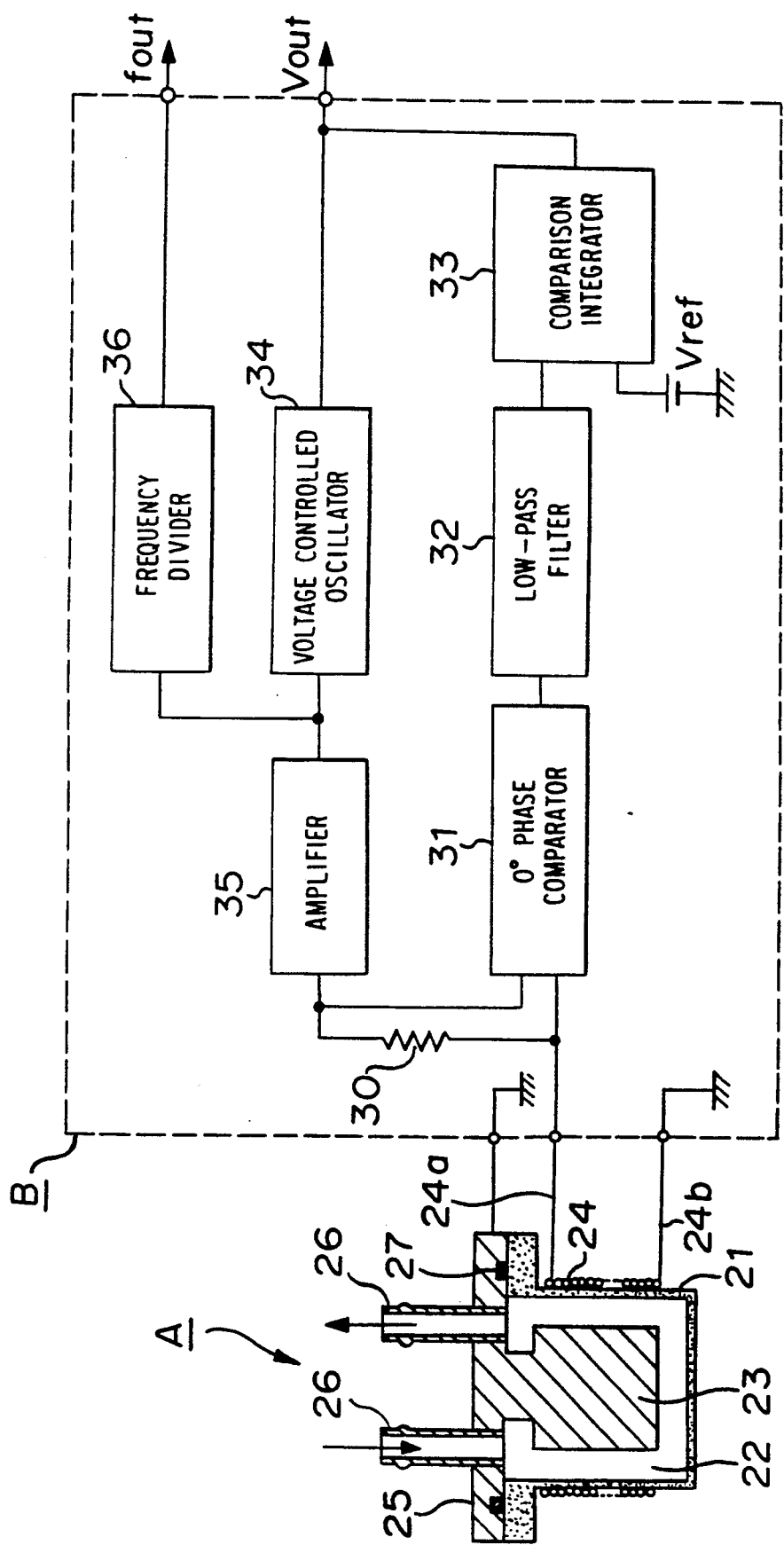
FIG. 5 is a diagram showing another embodiment of the dielectric constant detection apparatus for fuel according to the present invention.
Figure 6:
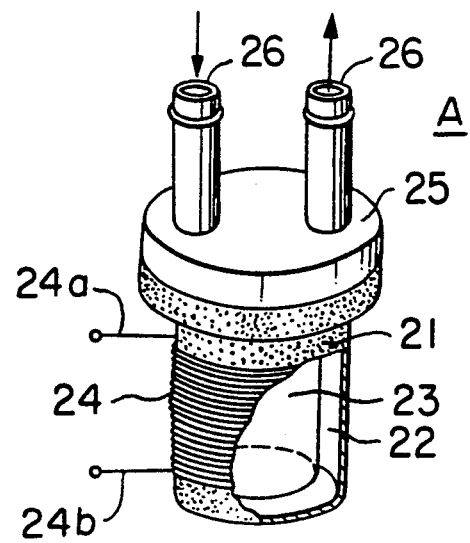
FIG. 6 is a perspective view partly broken of an embodiment of the sensor member used for the present invention.

In FIGS. 5 and 6, a symbol A indicates a sensor member, reference numeral 21 designates a cylindrical container-like insulation tube made of an insulation material such as ceramics, oil-resisting plastics or the like and adapted to introduce fuel to the inside of it, numeral 23 designates an electrically conductive electrode in a cylindrical shape which is disposed at the inner portion of the insulation tube 21 wherein the cylindrical face of the electrode is substantially parallel to the cylindrical face of the insulation tube 21 and the center axis of the electrode is the same as the insulation tube. Preferably, the electrode 23 is made of titanium, stainless steel, anodized aluminium. It is because such material is durable to fuel.

Numeral 24 designates a monolayer-wound coil which is wound on the outer side of the insulation tube 21 so as to oppose the electrode 23; 24a and 24b are respectively leads for the monolayer-wound coil 4, and 22 designates a fuel passage formed between the inner surface of the insulation tube on which the monolayer-wound coil 24 is formed and the outer circumferential surface of the cylindrical electrode 23. Numeral 25 designates a flange with which the electrode 23 is attached and which is connected to the insulation tube 21 through a fuel sealing member 27. Thus, a fuel container is formed of the above-mentioned elements. In this embodiment, the electrode 23 is formed integrally with the flange 25 with a terminal grounded. Numeral 26 designates a pair of nipples for introducing the fuel in the fuel passage 22, which penetrate the flange 25.

A symbol B indicates a detection circuit section in which numeral 30 designates a resistor connected in series to the monolayer-wound coil 24 and the lead 24a to thereby form a series circuit, and numeral 31 designates a 0° phase comparator for receiving a signal appearing at the connecting portion of the coil 24 and the resistor 30 and a signal appearing at the other end of the resistor 30, i.e. a signal applied to the series circuit.

Numeral 32 designates a low-pass filter to which the output of the 0° phase comparator 31 is connected, numeral 33 designates a comparison integrator for receiving the output of the low-pass filter 32 and a predetermined reference voltage $V_{ref}$ which corresponds to a phase of 0°, numeral 34 designates a voltage controlled oscillator to which the output of the comparison integrator 33 is connected, and numeral 35 designates an amplifier for amplifying the output of the voltage controlled oscillator 34. The output terminal of the amplifier is connected to the series circuit. Numeral 36 designates a frequency divider for dividing the output frequency of a signal generated from the voltage controlled oscillator 34.

The function of the third embodiment will be described wherein the detection apparatus of the embodiment is used for detecting the methanol content of methanol blended gasoline.

Figure 7:
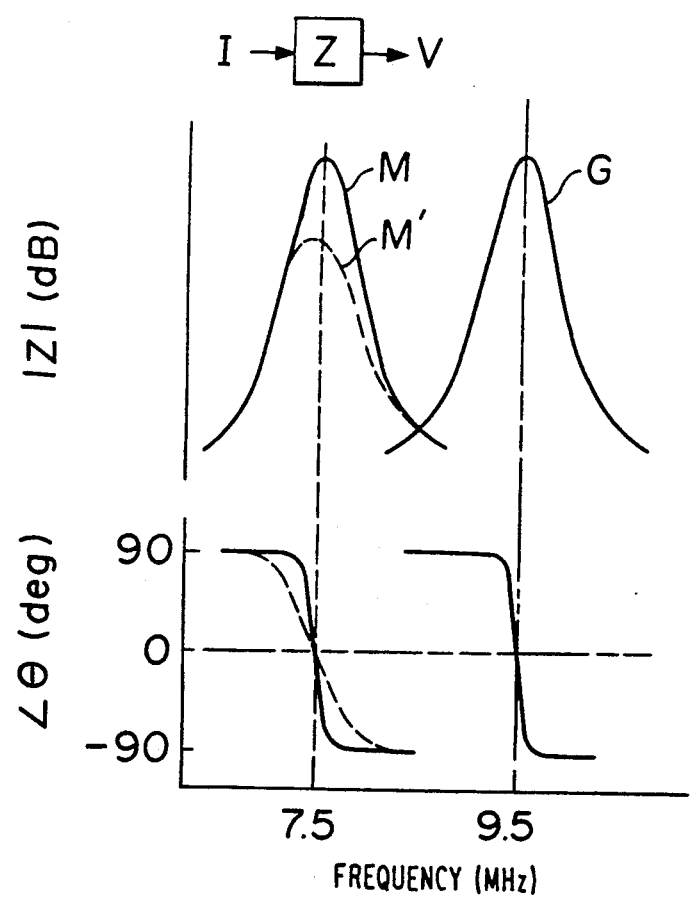
FIG. 7 is a characteristic diagram showing a relation of frequency to the impedance of the sensor member.

FIG. 7 is a diagram showing the frequency characteristics of the impedance Z of the sensor member including the monolayer-wound coil 24 as shown in FIG. 6 wherein gasoline G or methanol M (M' represents a case that impurities are contained) is used for fuel to be introduced in the fuel passage 22, and the frequency of a high frequency signal applied across the leads 24a, 24b of the coil 24 is changed.

When the frequency of a harmonic wave signal applied to the coil 24 is changed, an LC parallel resonance takes place wherein the impedance Z is the maximum at a specified frequency and a current-voltage phase $<\theta 20$ is 0° is resulted because of the self-inductance L of the coil 24 and the capacitance C between the coil 24 and the electrode 23.

The resonance frequency f is substantially equivalent to the before-mentioned formula (1). Namely, the resonance frequency f relys on the dielectric constant $\epsilon$ of the fuel introduced in the fuel passage 22 formed between the monolayer-wound coil 24 and the electrically conductive electrode 23. As the dielectric constant $\epsilon$ becomes large, namely, for instance, in methanol blended fuel consisting of gasoline having a dielectric constant $\epsilon = 2$ and methanol having a dielectric constant $\epsilon = 33$, the resonance frequency decreases as the methanol content is high. As described above, the symbols k, a and b in the formula (1) are constants which are determined by the shape of the sensor member A in the same manner as the conventional apparatus. Namely, they are determined by, for instance, the diameter and the wall thickness of the insulation tube 21, the dielectric constant for a material constituting the insulation tube 21, the distance between the electrode 23 and the coil 24, the self-inductance L of the coil 24 and so on.

In the next, description will be made in more detail as to a method of detecting such resonance frequency.

A high frequency signal is supplied from the amplifier 35 to the series circuit formed of the resistor 30 and the coil 24 while methanol blended gasoline is passed in the fuel passage 22. A signal appearing at both ends of the resistor 30, i.e. a voltage signal applied to the series circuit and a voltage signal applied to the coil 24 are inputted to the 0° phase comparator 31 so that the phase difference of the both signals are compared. The comparison of the phase difference of the voltage signals is equivalent to the comparison of the current-voltage phase $<\theta°$ of the impedance as shown in FIG. 7.

If a sine wave amplifier is used for the amplifier 35 so that a sine wave can be obtained for the high frequency signal to be applied to the series circuit, the voltage signal becomes a sine wave too. In this case, accordingly, the 0° phase comparator 31 may be a multiplier.

The 0° phase comparator 11 outputs a signal corresponding to the phase difference between the above-mentioned signals. The low-pass filter 32 outputs a d.c. voltage signal proportional to the phase difference. The comparison integrator 33 compares and integrates the reference voltage $V_{ref}$ which corresponds to the output of a signal having a phase of 0° from the low-pass filter 32 and the output of the low-pass filter 33. The voltage output of the comparison integrator 33 is inputted to the voltage controlled oscillator 34 by which the frequency of the high frequency signal applied to the series circuit through the amplifier 35 is determined. Namely, a phase synchronizing loop is constituted by the series circuit and the circuits indicated by the numerals 31-35 so that the oscillation frequency of the voltage controlled oscillator 34 is controlled in such a manner that the phase difference between the voltage signal applied to the series circuit and the voltage signal applied to the monolayer-wound coil 24 becomes 0°. Accordingly, the voltage output $V_{out}$ of the comparison integrator 33 or the frequency output of the voltage controlled oscillator 34 corresponds to a value corresponding to the parallel resonance frequency of the sensor member, namely, the dielectric constant $\epsilon$ of the fuel, or in other words, the methanol content.

The output frequency of the voltage controlled oscillator 34 depends also on the size of the sensor member A. In the embodiment having a small-sized shape as shown in FIG. 6, however, a high frequency signal having several MHz is used (FIG. 7) and accordingly, the frequency is divided by the frequency divider 36 so that a signal having a frequency suitable for measurement is generated as a frequency output $f_{out}$.

Figure 8:
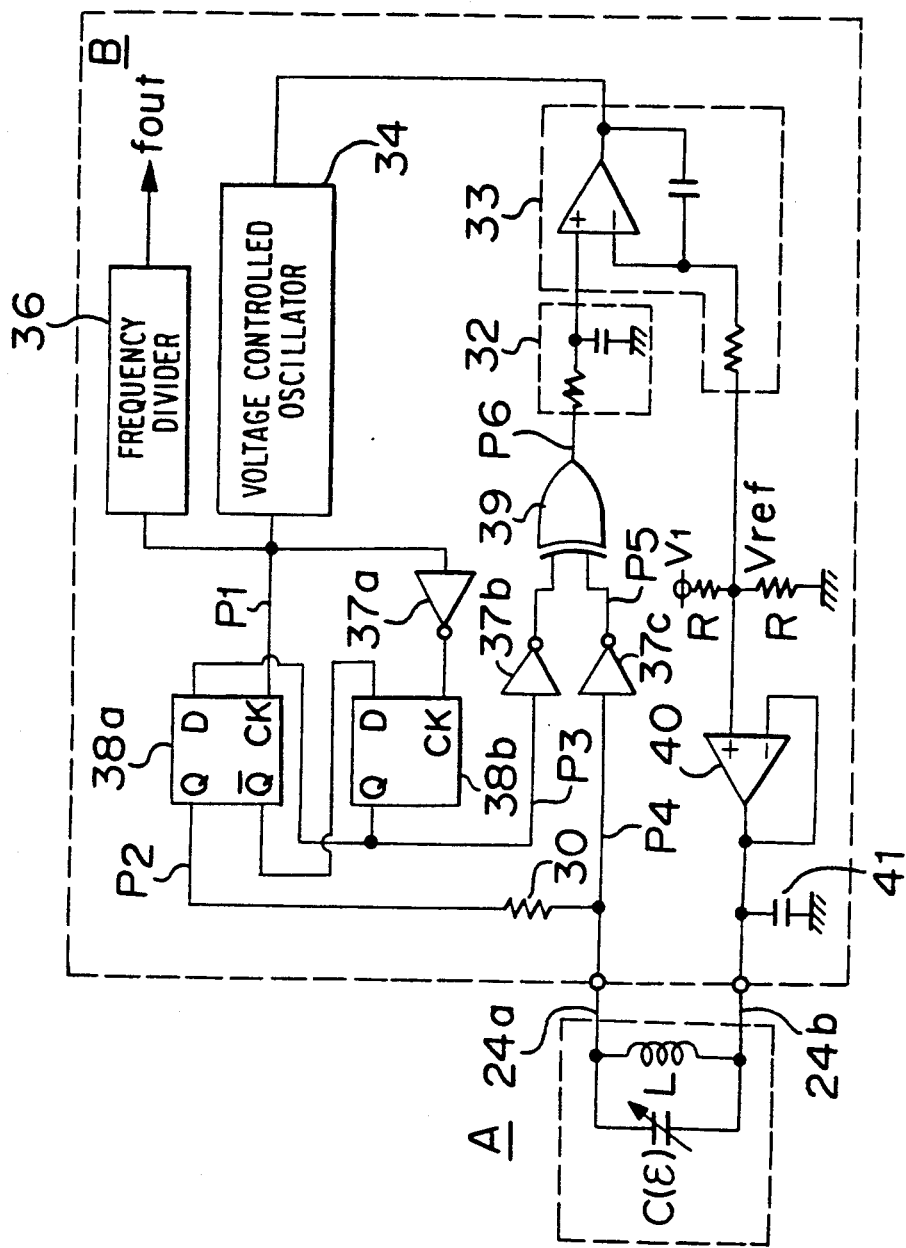
FIG. 8 is a diagram showing a concrete example of a detection circuit used for the present invention.
Figure 9:
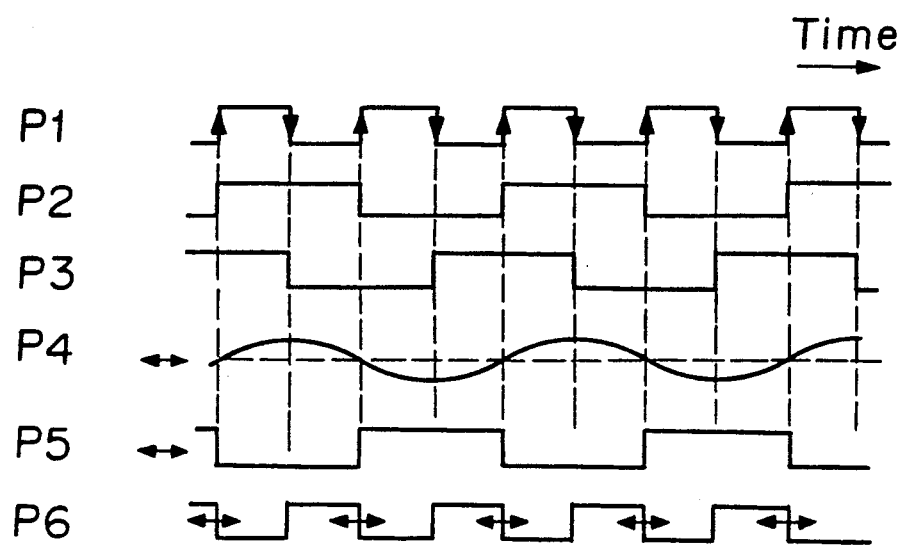
FIG. 9 is a time chart diagram for the detection circuit.

FIG. 8 shows more in detail the detection circuit B in which the phase synchronizing loop is formed so that the phase difference between the voltage signal applied to the series circuit and the voltage signal applied to the coil 24 becomes 0° by using an exclusive OR circuit 39. In FIG. 8, the same reference numerals as in FIG. 5 designate the same or corresponding parts, and therefore, description of these parts is omitted. FIG. 9 shows time charts of signals P1-P6 appearing at elements in the circuit.

In FIG. 8, the construction of the sensor member A is the same as that of the sensor member A in FIG. 5. Numerals 37a-37c designate inverter circuits, numerals 38a and 38b designate D flip-flop circuits (hereinbelow, referred to as D·FFs), numeral 40 designates an operation amplifier, and numeral 41 designates a direct current cutting capacitor.

In FIG. 8, a rectangular wave signal (P1) having a high frequency generated from the voltage controlled oscillator 34 is inputted into the CK port of the first D·FF 38a, and a signal which is formed by inverting the phase of the rectangular wave signal (P1) by the inverter circuit 37a is inputted to the CK port of the second D·FF 38b. A signal generated from the inversion output port $\overline{Q}$ of the first D·FF 38a is inputted to the D port of the second D·FF 38b, and a signal from the output port Q of the second D·FF 38b is inputted to the D port of the first D·FF 38a. Accordingly, the signal (P2) of the output port Q of the first D·FF 38a which is to be applied to the series circuit undergoes date renewal at each rising time of the rectangular wave signal (P1), whereby the signal (P1) is transformed into a signal which is subjected to ½ demultication.

On the other hand, a signal (P3) from the output port Q of the second D·FF 38b, which is to be inputted to a terminal of the exclusive OR circuit 39 through the inverter circuit 37b undergoes data renewal at the falling time of the signal (P1), whereby it is transformed into a signal which has the same frequency as the signal (P2) and a phase difference of 90°. The other input terminal of the exclusive OR circuit 39 receives a voltage signal (P4) applied to the connecting point of the resistor 30 and the coil 24 through the inverter circuit 37c, and the signal is compared with a signal whose phase is inverted from the signal (P3).

In this embodiment, since the voltage signal (P4) produced in the coil 24 has a sine waveform as shown in FIG. 9, it is feasible that a power source voltage $V_s$ is divided to ½ by the resistor R, the divided voltage is controlled by the operation amplifier 40 followed by separating from the ground portion only the direct current component by means of the direct current cutting capacitor 41, and the direct current level is controlled in accordance with a level of judgment of the inverter circuit 37c. Thus, the inverter circuit 37c functions as a waveform shaping circuit, and accordingly, the output of the inverter circuit 37c becomes a rectangular wave signal whose phase is inverted from that of the signal (P2) in the LC resonance frequency, i.e. the rectangular wave signal has a phase which is reverse from the phase of the signal (P3) and is shifted by 90° from that of the signal (P3). In short, the duty of the output signal (P6) of the exclusive OR circuit 39 becomes 50% when the phase difference between the signal applied to the series circuit and the voltage signal applied to the monolayer-wound coil 24 is 0°, namely, the LC resonance frequency takes place. The waveforms of the signals P1-P6 when the phase difference of the signals is not 0° are shown in FIG. 9.

The output (P6) of the exclusive OR circuit 39 is inputted to the low-pass filter 32 and the direct current voltage of the filter 32 becomes ½ as much as the power source voltage $V_s$ at the resonance frequency. The direct current voltage is received by the comparison integrator 33 which has a reference potential $V_{ref}$ which is ½ as much as the power source voltage $V_s$, and the frequency of the voltage controlled oscillator 34 is controlled by the output of the comparison integrator 33. The detection circuit B functions as a phase synchronizing loop wherein the frequency of the signal of the voltage controlled oscillator 34 is controlled so that the phase difference between the signal applied to the series circuit and the voltage signal applied to the monolayer-wound coil 24 is 0°. Accordingly, the frequency output $f_{out}$ which is obtained by demultiplying the frequency of the signal of the voltage controlled oscillator 34 by the frequency divider 36, becomes a function which is linearly decreased with respect to the dielectric constant $\epsilon$ of fuel.

Figure 10:
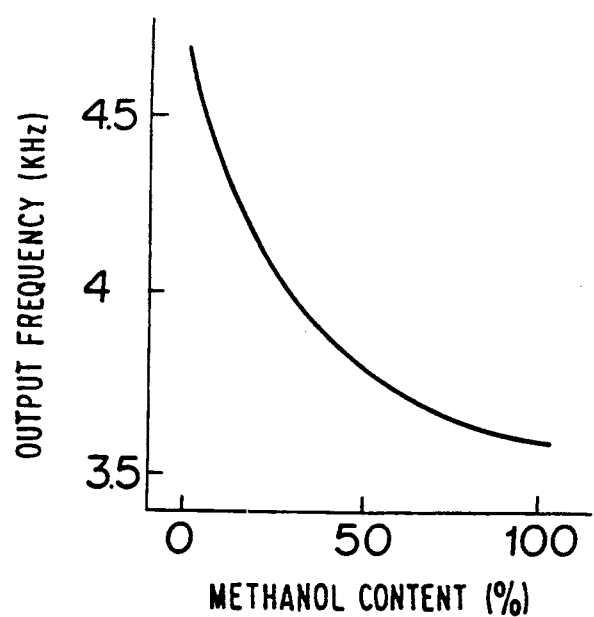
FIG. 10 is an output characteristic diagram of the detection circuit.

FIG. 10 is a diagram showing a relation of the frequency output $f_{out}$ to alcohol content in alcohol blended gasoline in an apparatus in which the detection circuit as shown in FIG. 8 is used. In FIG. 10, when the methanol content increases and the dielectric constant $\epsilon$ increases, the output decreases.

In the third embodiment of the present invention, even when the Q factor at the resonance point is decreased owing to the increase of the electric conductivity of fuel due to impurities contained in the fuel, or the reduction of the insulation resistance due to a change of the atmosphere such as temperature and humidity surrounding the sensor member A, there is no substantial influence to the resonance frequency at which the phase becomes 0° as indicated by the broken line in FIG. 7. Accordingly, there is little variation in the output unlike the conventional apparatus.

In the third embodiment, description has been made as to the case that the electrically-conductive electrode is disposed on the same axis as the monolayer-wound coil of the sensor member. However, the present invention is not always limited to that embodiment, and it is sufficient that there is a capacitance provided by fuel between the cylindrical face of a monolayer-wound coil and an electrically-conductive electrode. In the third embodiment of the present invention, it may be applied to detect the dielectric constant of liquid other than the methanol blended fuel in the same manner as the first and second embodiments.

In accordance with the third embodiment of the present invention, an electrically-conductive electrode and a monolayer-wound coil are disposed to form a fuel passage therebetween through which fuel is passed and a resistor is connected in series to the coil. A phase comparator, a low-pass filter, a comparison integrator and a voltage controlled oscillator are provided so that the frequency of the signal applied to the series circuit is feedback controlled, whereby the dielectric constant of the fuel is detected on the basis of the voltage output of the comparison integrator or the output frequency of the voltage controlled oscillator. Accordingly, the properties of the fuel can be detected with high accuracy regardless of the increase of the electric conductivity of the fuel due to impurities contained in the fuel and a change of the atmosphere such as temperature and humidity surrounding the sensor member.

We claim:

1. A detection apparatus for detecting a dielectric constant of fuel which comprises:
    an electrically conductive electrode (3) disposed adjacent to a fuel flow passage (2) and applied with an excitation signal,
    a monolayer-wound coil (4) disposed spaced at a predetermined distance from said electrode such that fuel is introduced in a space between said electrode and said coil,
    a phase comparator which receives the excitation signal to be applied to said electrode and an induced signal in said coil to thereby compare the signals, whereby the phase difference between the signals is detected,
    a low-pass filter to output the d.c. signal component of an output signal of the phase comparator,
    a comparison integrator connected to said low-pass filter to output a controlled output signal so that the phase difference between the excitation signal to be applied to said electrode and the induced signal in the coil becomes 90°, and
    a voltage controlled oscillator connected to said comparison integrator so that the frequency of a signal, to be applied to said electrode, of the voltage controlled oscillator is changed depending on the output signal of said comparison integrator, whereby the dielectric constant of the fuel is detected on the basis of a voltage output signal from said comparison integrator, or a frequency output signal from said voltage controlled oscillator.

2. The detection apparatus for detecting a dielectric constant of fuel according to claim 1, which further comprises means for maintaining the amplitude of the induced signal of said coil to be constant.

3. A detection apparatus for detecting a dielectric constant of fuel which comprises:
    an electrically conductive electrode (23) disposed adjacent to a fuel flow passage (22),
    a monolayer-wound coil (24) disposed apart from said electrode by a predetermined distance such that fuel is introduced in a space between said electrode and said coil,
    a resistor connected in series to said monolayer-wound coil to thereby form a series circuit,
    a signal application means for applying a high frequency signal to said series circuit,
    a phase comparator which receives a signal appearing at a connecting portion of said monolayer-wound coil and said resistor and the high frequency signal to be applied to the series circuit to thereby compare the signals, whereby the phase difference between both signals is detected,
    a low-pass filter to output the d.c. signal component of an output signal of the phase comparator,
    a comparison integrator connected to said low-pass filter to output a controlled output signal so that the phase difference between the signal appearing at the connecting portion of said monolayer-wound coil and said resistor, and the high frequency signal to be applied to said series circuit becomes 0°, and
    a voltage controlled oscillator connected to said comparison integrator so that the frequency of the high frequency signal to be applied to said series circuit is changed depending on the output signal of said comparison integrator, whereby the dielectric constant of the fuel is detected on the basis of a voltage output signal of said comparison integrator, or a frequency output signal of said voltage controlled oscillator.

* * * * *